United States Patent
Vautravers et al.

(10) Patent No.: US 11,104,634 B2
(45) Date of Patent: Aug. 31, 2021

(54) METHOD FOR PRODUCING 2-METHOXYACETIC ACID

(71) Applicant: BASF SE, Ludwigshafen am Rhein (DE)

(72) Inventors: Nicolas Vautravers, Ludwigshafen am Rhein (DE); Joaquim Henrique Teles, Ludwigshafen am Rhein (DE); Werner Pottgiesser, Ludwigshafen am Rhein (DE); Henning Althoefer, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 426 days.

(21) Appl. No.: 16/311,198

(22) PCT Filed: Jun. 22, 2017

(86) PCT No.: PCT/EP2017/065413
§ 371 (c)(1),
(2) Date: Dec. 19, 2018

(87) PCT Pub. No.: WO2018/001861
PCT Pub. Date: Jan. 4, 2018

(65) Prior Publication Data
US 2021/0188754 A1    Jun. 24, 2021

(30) Foreign Application Priority Data

Jun. 28, 2016 (EP) .................................... 16176637

(51) Int. Cl.
*C07C 51/00*     (2006.01)
*C07C 51/235*   (2006.01)
*B01J 21/18*     (2006.01)
*B01J 23/42*     (2006.01)

(52) U.S. Cl.
CPC ............. *C07C 51/235* (2013.01); *B01J 21/18* (2013.01); *B01J 23/42* (2013.01)

(58) Field of Classification Search
CPC .................................................... C07C 51/235
See application file for complete search history.

(56) References Cited

U.S. PATENT DOCUMENTS 3,342,858 A    9/1967  Fuhrmann et al.

FOREIGN PATENT DOCUMENTS

| CN | 104892390 A | 9/2015 |
|----|-------------|--------|
| DE | 2936123 A1  | 4/1981 |
| DE | 3135946 A1  | 3/1983 |
| DE | 3345807 A1  | 6/1985 |

OTHER PUBLICATIONS

International Search Report for PCT/EP2017/065413 dated Sep. 22, 2017.
Written Opinion of the International Searching Authority for PCT/EP2017/065413 dated Sep. 22, 2017.

*Primary Examiner* — Sikarl A Witherspoon
(74) *Attorney, Agent, or Firm* — Faegre Drinker Biddle & Reath LLP

(57) ABSTRACT

A method for producing 2-methoxyacetic acid by oxidizing 2-methoxyethanol in a reaction device using oxygen at a temperature of 20 to 100° C. and an oxygen partial pressure of 0.01 to 2 MPa in the presence of water and a heterogeneous catalyst containing platinum, in which the method is carried out semi-continuously or continuously, and 2-methoxyethanol is added to the reaction device in a temporally and/or spatially distributed manner such that temporally and spatially, the mass ratio of 2-methoxyethanol to 2-methoxyethanol plus water per volume element in the reaction device is constantly ≤0.80 of the mass ratio of the added 2-methoxyethanol to the added 2-methoxyethanol plus water.

10 Claims, 7 Drawing Sheets a)

b)

a)

b)

METHOD FOR PRODUCING 2-METHOXYACETIC ACID

CROSS-REFERENCE TO RELATED APPLICATIONS

Figure 1:
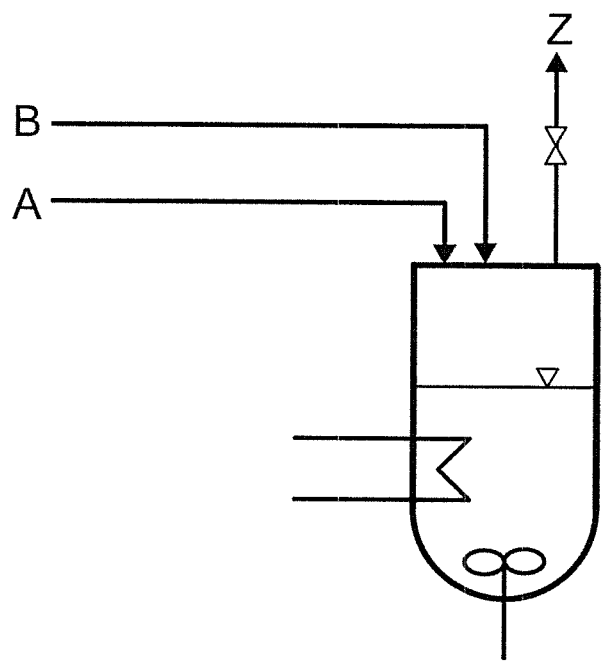
Figure 1:
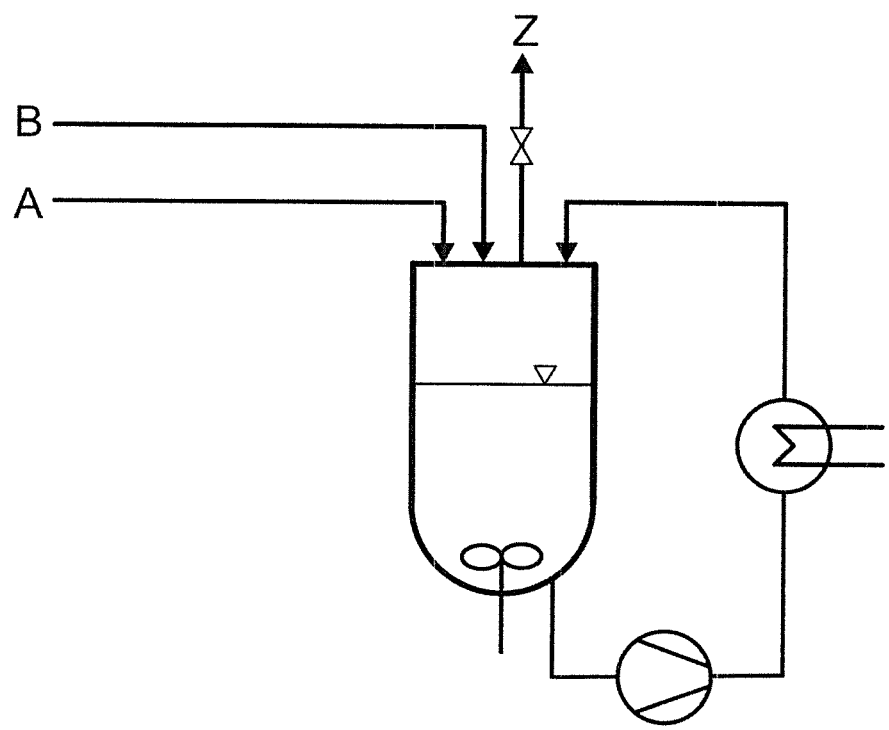

This application is a national stage application (under 35 U.S.C. § 371) of PCT/EP2017/065413, filed Jun. 22, 2017, which claims benefit of European Application No. 16176637.3, filed Jun. 28, 2016, both of which are incorporated herein by reference in their entirety.

The present invention relates to a method for producing 2-methoxyacetic acid by oxidizing 2-methoxyethanol in a reaction device using oxygen at a temperature of 20 to 100° C. and an oxygen partial pressure of 0.01 to 2 MPa in the presence of water and a heterogeneous catalyst containing platinum.

2-methoxyacetic acid is an important intermediate in chemical synthesis. By halogenation with phosgene or thionyl chloride, one can obtain therefrom e.g. 2-methoxyacetic acid chloride as a reactive synthesis building block. The latter substance is used for example in the synthesis of the fungicidal active compounds metalaxyl and oxadixyl.

2-methoxyacetic acid can be technically obtained e.g. by catalytic oxidation of 2-methoxyethanol.

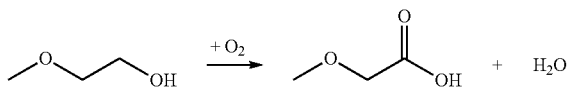

U.S. Pat. No. 3,342,858 generally describes the production of alkoxyacetic acids by oxidation of the corresponding alkoxyethanols using oxygen in the presence of water, a base such as e.g. sodium hydroxide, and a platinum-containing catalyst at a pH of >7 with formation of the corresponding alkoxyacetate salt, subsequent release of the alkoxyacetic acid by addition of an acid such as e.g. hydrochloric acid, and distillative production of the alkoxyacetic acid from the acidified reaction mixture.

The drawbacks of this method are the highly complex reaction concept, with formation of the corresponding alkoxyacetate salt as an intermediate, and subsequent release of the alkoxyacetic acid in a following step. This method requires the addition of a base followed by an acid as auxiliaries in respectively stoichiometric amounts. The salt necessarily formed from the added base and the added acid must be disposed of by complex means. In addition, fractionated distillation is required to isolate the alkoxyacetic acid. The yield of alkoxyacetic acid is only 50 to 90%.

DE 2936123 A teaches the production of alkoxyacetic acids by oxidation of the corresponding alkoxyethanols using oxygen in the presence of water and a platinum-containing catalyst at a pH of ≤7 with direct formation of the alkoxyacetic acid in the reaction mixture. The examples in DE 2936123 A relate to both the discontinuous and the continuous reaction mode.

In the discontinuous reaction mode in example 1 of the German document, a 15% aqueous 2-methoxyethanol solution and a catalyst with 5% Pt on activated carbon were first placed in a glass tube and fed through under normal atmospheric pressure and 45° C. oxygen. In this manner, a yield of 2-methoxyacetic acid of 95% was obtained.

In the continuous reaction mode in example 4 of the German document, a constant flow of a 20% aqueous 2-methoxyethanol solution was fed together with oxygen over a period of several weeks at 0.5 MPa and 48 to 53° C. through a stainless steel tube containing a catalyst with 10% Pt on activated carbon. The condensable portion of the reaction mixture was analyzed, and a yield of 2-methoxyacetic acid based on the reacted 2-methoxyethanol of over 90% was established. This corresponds computationally to the formation of up to 10% byproducts based on the reacted 2-methoxyethanol.

The drawback of this method is the obviously high content of byproducts, which on the one hand causes reactant loss and on the other requires complex processing of the reaction mixture.

CN 104892390 A also discloses the production of 2-methoxyacetic acid by oxidizing 2-methoxyethanol using oxygen in the presence of water and Pt/C as a catalyst. Examples 1 to 5 describe discontinuous operation, wherein in each case the Pt/C catalyst and an aqueous 2-methoxyethanol solution with a concentration of 2-methoxyethanol in the range of 32.4 to 49.0 wt % were placed in a reactor and then reacted with oxygen with varying pressure, temperature and reaction time. The reaction mixture obtained was distilled in each case in a vacuum in order to isolate the 2-methoxyacetic acid. In each case, a purity of 99% was obtained. The yield was in the range of 91 to 96%.

A drawback of this method is the required distillative separation of the 2-methoxyacetic acid in order to obtain a purity of at least 99%.

It was recognized according to the invention that the essential side reaction in catalytic oxidation of 2-methoxyethanol to 2-methoxyacetic acid is the formation of methoxyacetic acid-2-methoxyethylester.

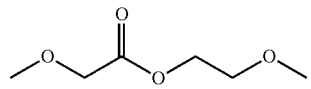

Methoxyacetic acid-2-methoxyethylester

In the context of the present invention, it was observed that in the methods according to the prior art, 2-methoxyethanol with a relatively high content of methoxyacetic: acid-2-methoxyethylester is obtained. For example, in an experimental comparative example in discontinuous operating mode in which the entire amount of 2-methoxyethanol was first placed in the reactor, a 2-methoxyethanol-discharge having a content of 2.6 wt % of methoxyacetic acid-2-methoxyethylester was obtained (comparative example 1).

Depending on the application of 2-methoxyacetic acid in question, however, even residual amounts of methoxyacetic acid-2-methoxyethylester in the lower percentage range have an adverse effect. There is therefore a great need to obtain 2-methoxyacetic acid with a content of methoxyacetic acid-2-methoxyethylester of 1.5 wt %.

Because of the boiling point level, it is indeed possible to separate water (boiling point 46° C. at 100 hPa) and unreacted 2-methoxyethanol (boiling point 54° C. at 100 hPa) relatively easily from 2-methoxyacetic acid (boiling point 125° C. at 100 hPa), but not from methoxyacetic acid-2-methoxyethylester (boiling point 123° C. at 100 hPa), as this substance has a boiling point only slightly below that of 2-methoxyacetic acid. Distillative separation of methoxyacetic acid-2-methoxyethylester from 2-methoxyacetic acid would be extremely complex, and would require use of a distillation column having a larger number of theoretical bottoms and the setting of a high reflux ratio. The operation of such a column would be also be relatively energy-intensive. Moreover, even in the case of an extremely large number of theoretical bottoms and a high reflux ratio, one would have to expect a loss of the 2-methoxyacetic acid target product. A negative property of 2-methoxyacetic acid that is not to be underestimated is its corrosiveness in combination with water. For this reason, the purification column would also have to be made of a corrosion-proof material, which entails considerable expense in providing the column. Finally, the methoxyacetic acid-2-methoxyethylester formed also represents a loss of 2-methoxyethanol and the 2-methoxyacetic acid target product.

In DE 3345807 A as well, the problems involved in obtaining 2-methoxyacetic acid by distillation from a mixture containing 2-methoxyacetic acid and methoxyacetic acid-2-methoxyethylester were recognized. As a solution, this German document proposes a completely different separation method, namely the slow crystallization of 2-methoxyacetic acid at a temperature below 8.5° C. By this method, 2-methoxyacetic acid can also be obtained from a solution with 4 wt % of methoxyacetic acid-2-methoxyethylester in a purity of 99.8 wt %. Methoxyacetic acid-2-methoxyethylester remains in the mother liquor.

Although the method proposed in DE 3345807 A makes it possible to obtain 2-methoxyacetic acid in high purity, it requires an additional method step in a crystallization apparatus. In addition to the provision of a crystallization apparatus and the complexity of carrying out crystallization, the method also requires the energy-intensive provision of a cooling medium for cooling the entire solution to a temperature below 8.5° C. The method is therefore relatively complex and energy-intensive.

The object of the present invention was therefore to provide a method for producing 2-methoxyacetic acid that avoids the drawbacks of the prior art, is based on readily available ingredients, is simple to carry out, forms 2-methoxyacetic acid with the highest possible selectivity, yield, and purity, and in particular, produces the byproduct methoxyacetic acid-2-methoxyethylester in a significantly lower amount than in the methods according to the prior art. In addition, despite the low formation of methoxyacetic acid-2-methoxyethylester compared to the prior art and thus higher selectivity for 2-methoxyacetic acid, the method is intended to require the lowest possible reaction volume and thus ideally provide a reaction mixture with the lowest possible concentration of 2-methoxyacetic acid. Moreover, the method should allow the simplest possible processing of the reaction mixture.

Surprisingly, a method was found for producing 2-methoxyacetic acid by oxidizing 2-methoxyethanol in a reaction device using oxygen at a temperature of 20 to 100° C. and an oxygen partial pressure of 0.01 to 2 MPa in the presence of water and a heterogeneous catalyst containing platinum, wherein the method is carried out semi-continuously or continuously, and the addition of 2-methoxyethanol to the reaction device is temporally and spatially selected such that temporally and spatially, in the liquid phase containing 2-methoxyethanol and 2-methoxyacetic acid in the reaction device, the quotient of CR/CA is constantly ≤0.80,
wherein CR is defined as $$CR = \frac{C(2-\text{methoxyethanol reactor})}{C(2-\text{methoxyethanol reactor}) + C(\text{water reactor})},$$

and wherein C(2-methoxyethanol reactor) denotes the mass of 2-methoxyethanol per volume element of the liquid phase containing 2-methoxyethanol and 2-methoxyacetic acid, and C(water reactor) denotes the mass of water per volume element of the liquid phase containing 2-methoxyethanol and 2-methoxyacetic acid,
in the semi-continuous method, CA is defined as $$CA = \frac{MT(2-\text{methoxyethanol total mass})}{MT(2-\text{methoxyethanol total mass}) + MT(\text{water total mass})},$$

wherein MT(2-methoxyethanol total mass) denotes the total mass of 2-methoxyethanol used in the semi-continuous method and MT(water total mass) denotes the total mass of water used in the semi-continuous method, and
in the semi-continuous method, CA is defined as $$CA = \frac{MF(2-\text{methoxyethanol mass flow})}{MF(2-\text{methoxyethanol mass flow}) + MF(\text{water mass flow})},$$

wherein MF(2-methoxyethanol mass flow) denotes the mass flow of 2-methoxyethanol supplied to the reaction device, and MF(water mass flow) denotes the mass flow of water supplied to the reaction device.

In contrast to the known methods according to the prior art, the method according to the invention, with addition of the same amount of 2-methoxyethanol and using the same reactor volume, results in a reaction mixture with higher purity of 2-methoxyacetic acid and in particular a significantly lower content of undesirable methoxyacetic acid-2-methoxyethylester. This surprising result is achieved by the addition according to the invention of 2-methoxyethanol, wherein the 2-methoxyethanol is added temporally and spatially to the reaction device such that temporally and spatially, in the liquid phase containing 2-methoxyethanol and 2-methoxyacetic acid in the reaction device, the quotient of CR/CA is constantly ≤0.80.

The term reaction device is to be understood as referring to the apparatus unit that comprises the reactor or optionally a plurality of mutually connected reactors including the required heat exchanger devices for cooling or heating and any devices for partial recycling of the reaction mixture.

The value CR is defined as $$CR = \frac{C(2-\text{methoxyethanol reactor})}{C(2-\text{methoxyethanol reactor}) + C(\text{water reactor})},$$

wherein C(2-methoxyethanol reactor) denotes the mass of 2-methoxyethanol per volume element of the liquid phase containing 2-methoxyethanol and 2-methoxyacetic acid, and C(water reactor) denotes the mass of water per volume element of the liquid phase containing 2-methoxyethanol and 2-methoxyacetic acid. The value CR thus denotes the concentration of 2-methoxyethanol in the liquid phase containing 2-methoxyethanol and 2-methoxyacetic acid in the reaction device, based on the concentration of 2-methoxyethanol and water in the reaction device. CR thus corresponds to the mass of 2-methoxyethanol based on the mass of 2-methoxyethanol and water. The value CR is therefore generally dependent on time and location. Depending on the progress of the reaction, the respective concentrations C(2-methoxyethanol reactor) and C(water reactor) vary depending on the reaction time and the site in the reaction device, and thus so does the value CR.

In the case of the value CA, one must distinguish whether the method is carried out semi-continuously or continuously.

Characteristic of the semi-continuous reaction mode is the addition of a specified amount of 2-methoxyethanol to the reaction device during the reaction, wherein no reaction mixture is removed from the reaction device during this period. It is possible either to add the entire amount of 2-methoxyethanol during the reaction or to first add a specified partial amount at the beginning and then add only the remaining amount during the reaction. With respect to the water, it is possible to first add the entire amount to the reaction device at the beginning, or at least a portion thereof, wherein the remaining portion is then added during the reaction. In carrying out the semi-continuous method, the amount of liquid in the reaction device increases because of the addition of 2-methoxyethanol and optionally of water. The reaction mixture can then subsequently be removed from the reaction device. The semi-continuous method is therefore carried out in individual lots, also referred to as batches. For the semi-continuous method, CA is defined as $$CA = \frac{MT(2-\text{methoxyethanol total mass})}{MT(2-\text{methoxyethanol total mass}) + MT(\text{water total mass})},$$

wherein MT(2-methoxyethanol total mass) denotes the total mass of 2-methoxyethanol used in the semi-continuous method, and MT(water total mass) denotes the total mass of water used in the semi-continuous method. In the semi-continuous method, the value CA therefore refers to total mass of 2-methoxyethanol used in the respective batch based on the total mass of 2-methoxyethanol and water used in the respective batch. The mass of any 2-methoxyethanol initially placed in the reactor is of course counted as part of the total mass of 2-methoxyethanol used. With respect to the water, both the mass of water initially present and the mass of any water added are to be taken into account, but not the mass of reaction water formed.

Characteristic of the continuous reaction mode is the continuous addition, averaged over time, of 2-methoxyethanol and water to the reaction device and the continuous removal, averaged over time, of reaction mixture from the reaction device. For the continuous method, CA is defined as $$CA = \frac{MF(2-\text{methoxyethanol mass flow})}{MF(2-\text{methoxyethanol mass flow}) + MF(\text{water mass flow})},$$

wherein MF(2-methoxyethanol mass flow) denotes the mass flow of 2-methoxyethanol supplied to the reaction device, and MF(water mass flow) denotes the mass flow of water supplied to the reaction device. As the reaction device is to be understood as a unit apparatus that already includes any possible devices for partial recycling of the reaction mixture, any flow of 2-methoxyethanol and/or water recycled due to partial recycling of the reaction mixture is therefore contained neither in MF(2-methoxyethanol mass flow) nor in MF(water mass flow). In the continuous method, therefore, the value CA is the mass of 2-methoxyethanol newly supplied to the reaction device per unit time based on the mass of 2-methoxyethanol and water newly supplied to the reaction device per unit time. Water formed during the reaction is also disregarded in calculating CA.

The corresponding temporal and spatial addition of 2-methoxyethanol to the reaction device is essential for the success of the method according to the invention. "Temporal" refers to the temporal distribution of addition during the reaction and "spatial" to the addition site of the reaction device. The term "constantly" makes it clear that the above-mentioned upper limit of the quotient of CR/CA in the liquid phase containing 2-methoxyethanol and 2-methoxyacetic acid in the reaction device is to be maintained at every site—i.e. spatially—and through the entire course of the method—i.e. temporally as well.

For example, temporally distributed addition can be carried out by supplying to the reaction device a specified amount of 2-methoxyethanol over a specified period of time. The supply can take place continuously or intermittently over this period of time. For example, an amount per unit time that increases or decreases during the period of time in question, wherein increasing and decreasing amounts can of course alternate, is also possible.

Temporally distributed addition is preferably carried out in the semi-continuous method. The distribution of the addition over a specified time period and the partial chemical conversion of previously added 2-methoxyethanol makes it possible to maintain the quotients of CR/CA in the liquid phase containing 2-methoxyethanol and 2-methoxyacetic acid in the reaction device at a value of ≤0.80 over the course of the reaction. In comparison to this, in a discontinuous method according to the prior art with complete addition of the entire amount of 2-methoxyethanol at the beginning of the reaction, the quotients of CR/CA would be calculated at 1.

For example, spatially distributed addition can take place by supplying 2-methoxyethanol at a specified site in the reaction device or distributed at various sites in the reaction device.

Spatially distributed addition is preferably carried out in the continuous method. By distributing the continuous addition over various supply sites along the spatial course of the reaction and the partial chemical conversion of 2-methoxyethanol added upstream of the respective addition site, it is possible to maintain the quotients of CR/CA in the liquid phase containing 2-methoxyethanol and 2-methoxyacetic acid in the reaction device at a value of 0.80 over the course of the reaction. In comparison to this, in a continuous method according to the prior art using a straight course in which 2-methoxyethanol is added only at a site at the spatial beginning of the reaction course, i.e. the site at which the 2-methoxyacetic acid first forms, the quotients of CR/CA would be calculated at 1.

The temporal and spatial course of CR can be determined in both semi-continuous and continuous operating mode, for example experimentally and in advance by means of simple experiments or calculated in advance if the reaction kinetics are known. For experimental determination, for example, the concentration of 2-methoxyethanol and water at various sites and various times over the course of the reaction in the reaction device can be analytically determined. The quantitative analysis can be carried out either at the desired site online or by sampling and subsequent offline analysis. 2-methoxyethanol, 2-methoxyacetic acid and water can be quantitatively determined, for example by gas chromatography, IR spectroscopy, NIR spectroscopy or $^1$H-NMR spectroscopy. Measurement of conductivity, dielectric constants, and impedance is also suitable for the quantitative determination of 2-methoxyacetic acid. Online analysis allows the current course of the reaction to be followed and thus also allows manual or automatic adjustment of the reaction conditions during the reaction, such as e.g. temperature, oxygen partial pressure or the amount of 2-methoxyethanol added per unit time and place. IR and NIR spectroscopy and measurement of conductivity, dielectric constants, and impedance in particular are suitable for the online analysis. For adjusting the reaction conditions during the reaction, however, it is not absolutely necessary in each case to determine the concentrations of 2-methoxyethanol, 2-methoxyacetic acid, and water. For this purpose, the online measurement of a characteristic measurement value, such as e.g. electrical conductivity, dielectric constants, or impedance, which then indirectly constitutes a measure of the course of the reaction, is sufficient in many cases. This measurement value can then for example regulate an automatic control loop that controls the addition of 2-methoxyethanol. It is also possible to further follow the course of the reaction indirectly by measuring the heat produced. For example, so-called calorimetry or the thermal balance can be advantageously used in following the semi-continuous method.

However, the value CA is predetermined in the semi-continuous method by the total amount of 2-methoxyethanol and water to be added, and in the continuous method by mass flow of 2-methoxyethanol and water to be added.

Preferably, in the method according to the invention, the addition of 2-methoxyethanol to the reaction device is temporally and spatially selected such that in the liquid phase containing 2-methoxyethanol and 2-methoxyacetic acid in the reaction device, temporally and spatially, the quotient of CR/CA is constantly ≤0.75, particularly preferably constantly ≤0.70, and most particularly preferably constantly ≤0.60. As a rule, the lower the quotient of CR/CA during the temporal and spatial course of the reaction, the less methoxyacetic acid-2-methoxyethylester is formed.

From an overall standpoint, however, in order to obtain the highest possible space-time yield, it is advantageous to select the addition of 2-methoxyethanol temporally and spatially at the beginning of the reaction course such that the quotient of CR/CA is in the upper area of the range according to the invention to the extent possible, i.e. is actually up to 0.80. As the course of the reaction progresses, the quotient of CR/CA naturally decreases and would be calculated as 0 in the event of full conversion of 2-methoxyethanol. However, in order to prevent the reaction time from becoming too long, the reaction is interrupted, as described a few paragraphs below, when a certain conversion rate of 2-methoxyethanol is reached. Here, the quotient of CR/CA is then ordinarily in the range of 0 to 0.1, preferably 0 to 0.05, and particularly preferably 0 to 0.02.

In contrast to the teaching of the present invention, in example 1 of DE 2936123 A, for example, the method was carried out discontinuously, and the entire amount of 2-methoxyethanol was placed in the reactor prior to the addition of oxygen. The quotient of CR/CA was thus 1 at the beginning of the reaction. In examples 1 to 5 of CN 104892390 A as well, using the discontinuous reaction mode, the quotient of CR/CA at the beginning of the reaction was also 1.

In example 4 of DE 2936123 A, the method was carried out continuously, with an aqueous 2-methoxyethanol solution being fed together with oxygen through a stainless steel tube. The quotient of CR/CA was therefore also 1 on the input side.

The method according to the invention thus clearly stands out compared to the prior art.

In the method according to the invention, the 2-methoxyethanol to be added can be supplied to the reaction device as a pure substance or in a mixture with further components. In selecting the further components, it is preferable to avoid components that have a negative effect on the conduct of the reaction and/or can only be separated from the reaction mixture with difficulty. In order to ensure the simplest possible processing, it is advantageous to use 2-methoxyethanol in the highest possible purity of 99 wt %, particularly preferably 99.5 wt %, and most particularly preferably 99.8 wt %.

Even when water is formed in a stoichiometric amount in the oxidation of 2-methoxyethanol according to the invention, water is already added at the beginning of the reaction as a solvent in order to provide 2-methoxyethanol in a dilute solution. This can be carried out for example by first preparing water or a mixture of water and 2-methoxyethanol at the beginning of the reaction. This is for example ordinarily the case in the semi-continuous method. In the continuous method, 2-methoxyethanol and water are ordinarily continuously added. Depending on the reaction mode, 2-methoxyethanol and water can be added separately or together as an aqueous 2-methoxyethanol solution.

The ratio by weight of water to 2-methoxyethanol, in the semi-continuous method based on the total masses of water and 2-methoxyethanol used and in the continuous method based on the mass flows of water and 2-methoxyethanol supplied to the reaction device, is in each case ordinarily ≥1.5, preferably ≥2, and ordinarily ≤10, preferably ≤5, and particularly preferably ≤3.

As a rule, it is possible to carry out the method according to the invention in the presence of a further solvent. This solvent should be inert under the present reaction conditions and should subsequently be easy to separate off. With respect to a simple reaction mode and processing and the objective of obtaining 2-methoxyethanol in the highest possible purity, however, it is preferable not to add any further solvent.

Oxygen is used either in pure form or diluted with other gases, for example in the form of air or an $O_2/N_2$ mixture. In order to keep the gas volume as low as possible at a predetermined oxygen partial pressure, the use of a gas having the highest possible oxygen content is advantageous. Preferably, therefore, an oxygen-containing gas is used having a content of ≥90 vol %, particularly preferably ≥95 vol %, most particularly preferably ≥99 vol %, and in particular ≥99.5 vol %.

In the method according to the invention, the oxygen partial pressure is 0.01 to 2 MPa, preferably ≥0.02 MPa and particularly preferably ≥0.1 MPa, and preferably ≤1 MPa and particularly preferably ≤0.3 MPa.

The oxidation according to the invention of 2-methoxyethanol is carried out at a temperature of 20 to 100° C., preferably ≥30° C. and particularly preferably ≥40° C., and preferably ≤80° C. and particularly preferably ≤60° C.

The heterogeneous catalyst to be used in the method according to the invention preferably contains platinum as a catalytic active component. The platinum is ordinarily fixed on a carrier. The widest possible variety of materials can be used as carriers. Examples include inorganic oxides such as e.g. aluminum oxide, zirconium oxide, titanium dioxide, silicon oxide, inorganic silicates such as e.g. aluminum silicate, carbon, or polymers. Of course, mixtures of various carrier materials can also be used. Carbon is preferably used as a carrier.

The catalyst generally comprises 0.1 to 10 wt %, particularly preferably ≥0.5 wt % and most particularly preferably ≥1 wt %, and particularly preferably ≤8 wt % and most particularly preferably ≤6 wt % of platinum, in each case based on the total mass of the heterogeneous catalyst.

Particularly preferably, in the method according to the invention, a heterogeneous catalyst containing 0.1 to 10 wt % of platinum on carbon is used.

The heterogeneous supported catalyst can be used in various geometric shapes and sizes, such as e.g. as a powder or a molded body. Powdered catalysts can be used for example in suspension mode. In fixed-bed mode, molded bodies such as e.g. granules, cylinders, hollow cylinders, spheres, or extrudates are preferably used. The molded bodies are then ordinarily fixed in the reactor according to known methods. In the case of catalyst molded bodies, these preferably have a mean particle size of 1 to 10 mm.

However, the catalyst is preferably used in the form of a powder. In such a case, the powdered catalyst is present in the reactor in suspension. In order to prevent discharge from the reaction system, a filter is ordinarily used to retain the suspension catalyst. The cross-flow filter can be mentioned as an example of a common suitable filter.

Independently of the geometric shape and size of the catalyst particles, the platinum is generally in the form of particles with a mean diameter of 0.1 to 50 nm, measured by x-ray diffraction. However, smaller or larger particles can also be present.

In production of the heterogeneous supported catalyst, the platinum is generally applied to the carrier by suitable methods.

Platinum is ordinarily applied to the carrier from solutions of suitable salts. Examples of suitable platinum salts include those soluble in aqueous or aqueous-acidic media and from which a platinum compound can be precipitated by increasing the pH. As preferred examples of a suitable platinum salt, one can mention platinum(II) nitrate, platinum(IV) chloride, and hexachloroplatinic acid hexahydrate. Examples of pH-increasing agents include in particular aqueous solutions of alkaline salts, such as e.g. alkali carbonates, preferably sodium carbonate.

In principle, the widest possible variety of methods can be used for applying the insoluble or sparingly soluble platinum compounds. In a preferred embodiment, the carrier is first placed in a suitable apparatus, for example a rotary drum or a stirred vessel, in a supernatant liquid such as water, and then mixed with the solution of the platinum salt and the pH-increasing solution. It is possible to first add the platinum salt followed by the pH-increasing solution, to first add the pH-increasing solution followed by the platinum salt, or to add both alternately or also at the same time.

Preferably, the carrier is first placed in water, and the pH is then adjusted using the pH-increasing solution to a value at which the platinum salt precipitates as an insoluble or sparingly soluble platinum compound. The solution of the platinum salt is then added while mixing, wherein the pH is maintained by further addition of the pH-increasing solution in a range in which the platinum salt precipitates as an insoluble or sparingly soluble platinum compound. The ratio by weight of the total amount of liquid to be added to the carrier is generally a value of 1 to 100.

After precipitation has occurred, the carrier containing the platinum compound is isolated, dried, and treated with hydrogen in order to reduce the platinum. Reduction can be carried out either using pure hydrogen or hydrogen diluted with an inert gas. Examples of suitable inert gases include nitrogen or noble gases.

In impregnation, the solution of a suitable platinum salt is sprayed onto the carrier in a suitable apparatus such as a rotary mixing drum. The total amount of platinum salt solution to be sprayed on is preferably at or below the liquid absorption capacity of the carrier used. In impregnation, platinum salts are preferably used that are converted by heat treatment into elemental platinum leaving no residue. Examples of platinum salts preferred for impregnation include platinum(II) nitrate and hexachloroplatinic acid.

The heterogeneous, supported catalyst generally has a BET surface area of $\geq 1$ m$^2$/g and $\leq 10,000$ m$^2$/g, determined according to DIN ISO 9277:2014-01. In the use of carbon as a carrier, the BET surface area is preferably in the range of $\geq 500$ m$^2$/g to $\leq 10,000$ m$^2$/g.

In the method according to the invention, it is generally also possible to use various catalysts along the spatial course of the reaction in one and the same reaction device. For example, it is even possible in cascaded or compartmented reactors to operate one section with a fixed-bed catalyst and another section with a suspension catalyst.

With respect to the amount of the catalyst to be used, the method according to the invention is highly flexible. As a rule, a higher content of platinum leads to higher catalytic activity, and one can thus as a rule convert more 2-methoxyethanol per unit time. In the semi-continuous method, the molar ratio of the total amount of 2-methoxyethanol used to the amount of platinum present in the reaction device is 1 to 10,000, preferably $\geq 10$ and particularly preferably $\geq 100$, and preferably $\leq 5000$ and particularly preferably $\leq 1000$. In the continuous method, the molar ratio of the amount of 2-methoxyethanol supplied to the reaction device per unit time to the amount of platinum present in the reaction device is 1 to 500 per h, preferably $\geq 5$ per h and particularly preferably $\geq 20$ per h, and preferably $\leq 300$ per h and particularly preferably $\leq 200$ per h.

In the semi-continuous method, 2-methoxyethanol is ordinarily supplied to the reaction device over a period of 1 to 10 h, preferably $\geq 2$ h, and preferably $\leq 6$ h. As needed, however, significant deviations from the above-mentioned target values are also possible. It is also explicitly mentioned that the amount of 2-methoxyethanol added can also be irregular, for example intermittent, increasing, decreasing, or fluctuating. Reference is made to the above embodiments with respect to the temporal and spatial course of the quotient of CR/CA throughout the reaction. After the addition of 2-methoxyethanol is completed, the reaction mixture is generally allowed to stand for a further period of time under reaction conditions in order to allow secondary reaction of as yet unreacted 2-methoxyethanol, and only after this is it further processed. In the semi-continuous method, the entire reaction time from the beginning of the reaction is ordinarily 2 to 20 h, preferably $\geq 9$ h, and more preferably s $\leq 14$ h.

In the continuous method, 2-methoxyethanol and water are supplied to the reaction device such that the mass flow of 2-methoxyethanol and water based on the total reactor volume in the reaction device is ordinarily 0.05 to 0.5 per h, preferably $\leq 0.11$ per h, and preferably $\geq 0.07$ per h.

The reaction time is primarily determined by the desired conversion rate. As a rule, the longer the reaction time under otherwise comparable conditions, the higher the conversion rate of 2-methoxyethanol as well. However, as unreacted 2-methoxyethanol can be relatively easily separated out and recycled or reused in a subsequent batch, it is quite advantageous for the purpose of efficient operation not to strive for full conversion, but to deliberately aim for partial conversion. This allows a higher conversion rate of 2-methoxyethanol per unit time and reactor volume to be achieved. For this reason, it is advantageous to aim for a conversion rate of 2-methoxyethanol of only 80 to 99%, preferably $\geq 90$% and particularly preferably $\geq 93$%, and preferably $\leq 98$% and particularly preferably $\leq 97$%.

In principle, suitable reaction apparatuses for the reaction device in the method according to the invention include those which are suitable for carrying out exothermic, heterogeneously catalyzed gas-liquid reactions and can be operated semi-continuously or continuously. One can mention as examples stirred vessels, trickle-bed reactors, bubble column reactors, jet loop reactors and cascades of the above-mentioned reactors. In the semi-continuous method, stirred vessels, trickle-bed reactors, and bubble column reactors are preferred, and in the continuous method, stirred vessel cascades, trickle-bed reactor cascades, cascaded bubble column reactors, and cascaded jet loop reactors are preferred. The reactor cascades generally used in the continuous method ordinarily contain 2 to 10, preferably 2 to 6, and particularly preferably 2 to 4 reactors connected in sequence. In the case of a cascaded bubble column reactor or a cascaded jet loop reactor, these generally have 2 to 8, preferably 2 to 5, and particularly preferably 2 to 3 compartments connected in sequence.

As mentioned above, the so-called reaction device is composed of the reactor or multiple interconnected reactors together with the heat exchanger devices and any devices for partial recycling of the reaction mixture.

Because of the high corrosiveness of aqueous 2-methoxyacetic acid, it is advisable for the reaction device, or at least the parts thereof that come into direct contact with the aqueous 2-methoxyacetic acid, to be composed of a corrosion-resistant material. Examples of suitable materials include high-alloy stainless steels, nickel-based alloys, titanium or titanium-palladium alloys, zircon, or tantalum. The use of high-alloy stainless steels is preferred. Alternatively, it is also possible to line the parts of the apparatus in question. For example, acid-resistant plastics or enamel are conceivable.

The reaction device is ordinarily equipped with a heat exchanger device. This is used before the beginning of the reaction for heating and during the reaction for dissipating the heat produced and thus for maintaining the desired reaction temperature. Depending on the configuration, the heat exchanger device can be inside or outside the reactor. If it is inside, it is ordinarily in the form of heat exchanger tubes or heat exchanger plates. Particularly advantageous is the use of a heat exchanger device outside the reactor. In this case, during operation, a flow of liquid is continuously removed from the reactor, fed to the external heat exchanger device, and then returned to the reactor. Regardless of whether the heat exchanger device is internal or external, it is preferably dimensioned such that it is capable of dissipating the maximum heat produced during the course of the reaction, thus preventing the desired reaction temperature from being exceeded.

For pressure maintenance and the selective removal of exhaust gas, such as e.g. carbon dioxide, which may form due to overoxidation, or inert gases brought in via the supply of oxygen-containing gas, the reaction device preferably comprises a pressure-holding valve. By means of this valve, the reaction pressure is limited to the desired maximum level, and when this maximum level is reached, exhaust gas is discharged from the reaction device.

The reaction mixture obtained in the method according to the invention of course comprises, in addition to the 2-methoxyacetic acid formed, water, unreacted 2-methoxyethanol, small amounts of methoxyacetic acid-2-methoxyethylester, and small amounts of further byproducts. This reaction mixture is then processed in order to obtain the purest 2-methoxyacetic acid possible. Here, the major advantage of the invention can be seen. As 2-methoxyacetic acid with a significantly lower content of undesirable methoxyacetic acid-2-methoxyethylester is formed by the addition according to the invention of 2-methoxyethanol to the reaction device, it is sufficient in many cases to remove only the low boilers water and 2-methoxyethanol by evaporation from the reaction mixture obtained. The 2-methoxyacetic acid thus obtained comprises according to the invention only small amounts of methoxyacetic acid-2-methoxyethylester and can often be directly used without further processing as a synthesis building block in subsequent reactions.

The evaporation of the low boilers water and 2-methoxyethanol can be carried out for example in a Sambay evaporator or a distillation column. Depending on the construction of the reactor used, it is even optionally possible to carry out evaporation of the low boilers water and 2-methoxyethanol directly in the reactor after termination of the reaction.

In order to carry out evaporation of the low boilers water and 2-methoxyethanol with the lowest possible energy input, said evaporation is preferably carried out at atmospheric pressure or under a vacuum, and particularly preferably under a vacuum.

However, if an even higher-purity 2-methoxyacetic acid is to be obtained, the product obtained after evaporation of the low boilers water and 2-methoxyethanol can be further purified. As distillative separation of 2-methoxyacetic acid and methoxyacetic acid-2-methoxyethylester is relatively complex due to their highly similar melting points, alternative methods are primarily suitable for this purpose. An example of an alternative possibility is the crystallization described in DE 3345807 A.

By means of simple evaporation of the low boilers water and 2-methoxyethanol, 2-methoxyacetic acid can be obtained in a purity of 99 wt %. Depending on how addition of the 2-methoxyethanol to the reaction device is carried out, it is even possible to achieve a purity of 99.5 wt % in a simple manner. As a rule, the lower the quotient of CR/CA, the less methoxyacetic acid-2-methoxyethylester is formed, and the purer the 2-methoxyacetic acid is.

In the following, several possible embodiments of the method according to the invention are explained. In FIGS. 1 to 7, the following abbreviations are used:

A 2-methoxyethanol (optionally as an aqueous solution)
B oxygen
C water
M reaction mixture
Z exhaust gas (pressure-controlled)

Semi-continuous operation is preferably carried out in a stirred vessel, a trickle-bed reactor, or a bubble column reactor.

FIGS. 1a and 1b show a highly simplified diagram of possible reaction devices for carrying out the semi-continuous method using a stirred vessel. In FIG. 1a, the heat exchanger device is inside the stirred vessel, and in FIG. 1b it is outside. The stirred vessel can be operated both in suspension mode and in fixed-bed mode. It is preferably operated in suspension mode. At the beginning of the reaction, water and the catalyst are ordinarily first placed in the stirred vessel. Moreover, it is also possible to place a portion of the 2-methoxyethanol to be used in the vessel at the beginning. The reaction device is now set to reaction conditions, i.e. in particular, it is brought to the desired temperature via mixing, and the desired oxygen partial pressure is set by pressurization of oxygen. 2-methoxyethanol is then supplied via an inlet tube or a nozzle in a temporally distributed manner until the entire mass of 2-methoxyethanol to be added is reached. Depending on the variant, it is also possible to supply an aqueous 2-methoxyethanol solution. In order to maintain the desired oxygen partial pressure, oxygen is replenished during the reaction. Oxygen can also be added for example through an inlet tube or a nozzle. Excess gas can for example be discharged via pressure maintenance. After addition of the 2-methoxyethanol is completed, it is advantageous as a rule to leave the reaction mixture standing for a certain period so that it will undergo a secondary reaction in order to increase the conversion rate under the reaction conditions. As a rule, the reaction device is then expanded and emptied, and the reaction mixture is processed.

Figure 2:
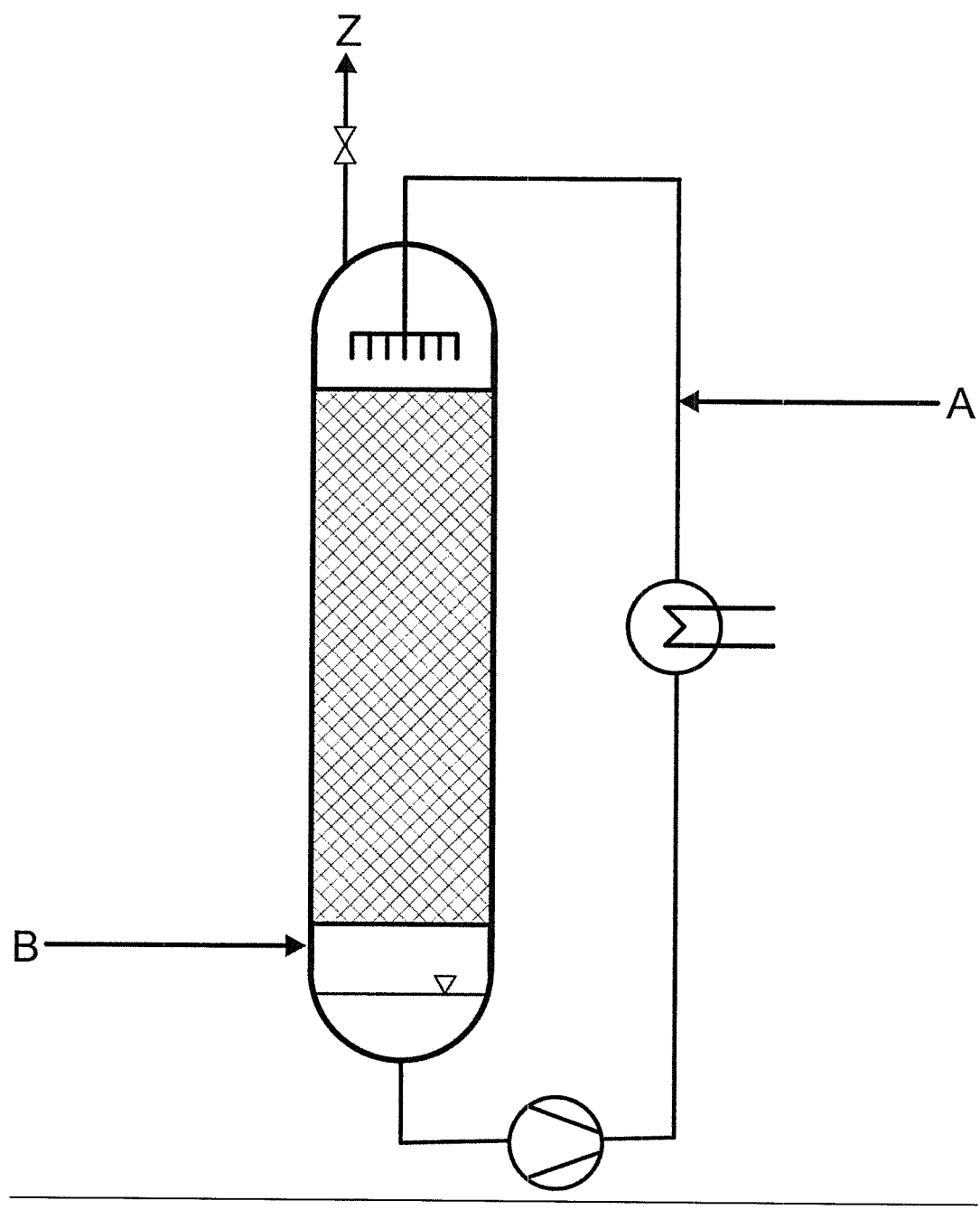

FIG. 2 shows a highly simplified diagram of a possible reaction device for carrying out the semi-continuous method using a trickle-bed reactor. This is advantageously equipped with an external heat exchanger. The trickle-bed reactor can be operated both in suspension mode and in fixed-bed mode. In the case of suspension mode, an inert filling or an inert packing is used as a trickle bed. Operation in fixed-bed mode is preferred. At the beginning of the reaction, water and the catalyst are ordinarily first placed in the trickle-bed reactor. The reaction device is now set to reaction conditions, i.e. in particular, it is brought to the desired temperature via the external heat exchanger circuit, and the desired oxygen partial pressure is set by pressurization of oxygen. 2-methoxyethanol is then temporally distributed to the reaction device until the entire mass of 2-methoxyethanol to be added is reached. As the liquid phase is virtually completely backmixed because of the heat exchanger circuit, 2-methoxyethanol can as a rule be added everywhere in the reaction device. Preferably, however, the supply takes place in the heat exchanger circuit. Depending on the variant, it is also possible to supply an aqueous 2-methoxyethanol solution. In order to maintain the desired oxygen partial pressure, oxygen is replenished during the reaction. The addition of oxygen preferably takes place below the trickle bed. Alternatively, however, oxygen can also be added at other sites, for example at the reactor head. In order to maintain the desired oxygen partial pressure, oxygen is replenished as needed during the reaction. Excess gas can for example be discharged via pressure maintenance. During the reaction, the trickle bed is supplied via nozzles that are located above the trickle bed and through which the reaction mixture flows from the external heat exchanger. In operation of the trickle-bed reactor, the liquid level is below the trickle bed. The flow for the heat exchanger circuit is removed from the area referred to as the bottom area. After addition of the 2-methoxyethanol is completed, it is advantageous as a rule to leave the reaction mixture standing for a certain period so that it will undergo a secondary reaction in order to increase the conversion rate under the reaction conditions. As a rule, the reaction device is then expanded and emptied, and the reaction mixture is processed.

Figure 3:
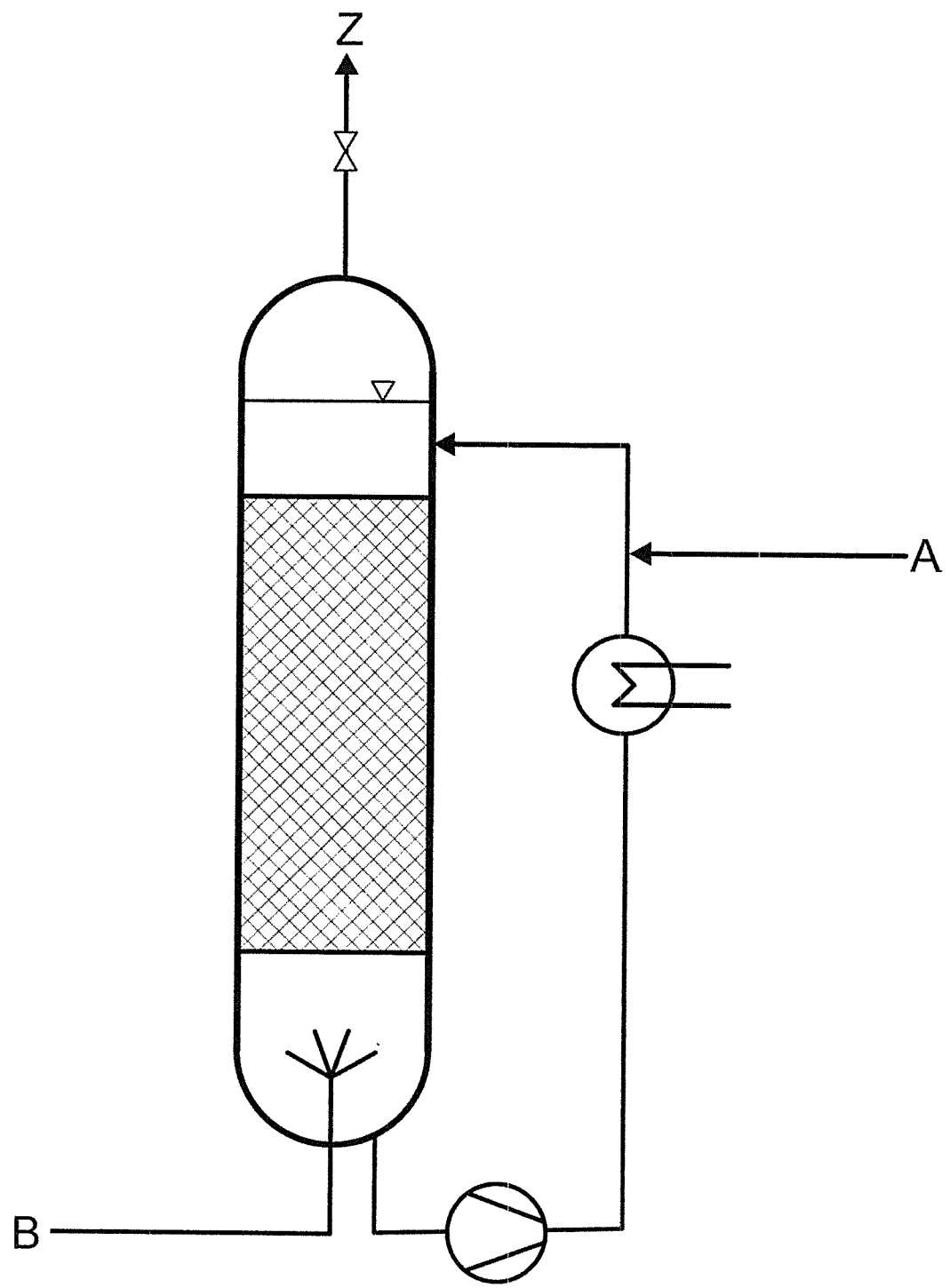
Figure 4:
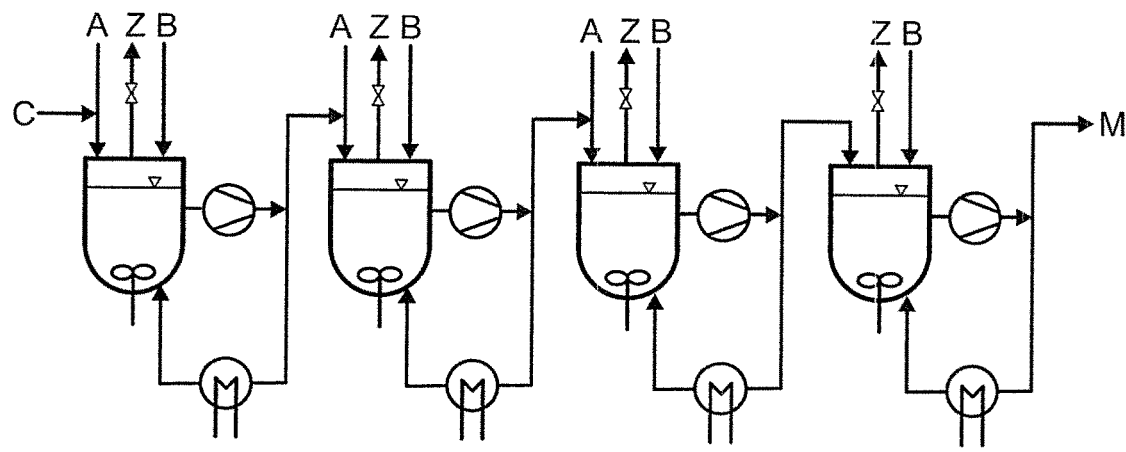
Figure 4:
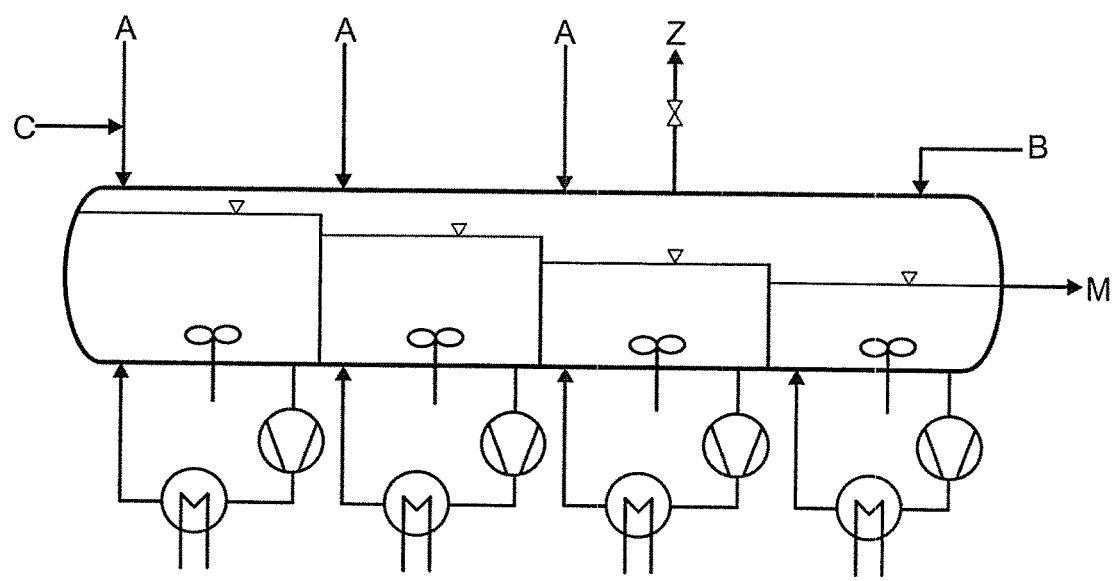

FIG. 3 shows a highly simplified diagram of a possible reaction device for carrying out the semi-continuous method using a bubble column reactor. This is also advantageously equipped with an external heat exchanger. The bubble column reactor can also be operated both in suspension mode and in fixed-bed mode. In the case of suspension mode, an inert filling or an inert packing can optionally be used as a mixing element. Operation in fixed-bed mode is preferred. At the beginning of the reaction, water and the catalyst are ordinarily first placed in the bubble column reactor. The reaction device is now set to reaction conditions, i.e. in particular, it is brought to the desired temperature via the external heat exchanger circuit, and the desired oxygen partial pressure is set by pressurization of oxygen. 2-methoxyethanol is then temporally distributed to the reaction device until the entire mass of 2-methoxyethanol to be added is reached. As the liquid phase is virtually completely backmixed because of the heat exchanger circuit, 2-methoxyethanol can as a rule be added everywhere in the reaction device. Preferably, however, the supply takes place in the heat exchanger circuit. Depending on the variant, it is also possible to supply an aqueous 2-methoxyethanol solution. In order to maintain the desired oxygen partial pressure, oxygen is replenished during the reaction. The addition of oxygen is carried out via one or a plurality of nozzles installed below the mixing element. Excess gas can for example be discharged via pressure maintenance. Liquid reaction mixture is ordinarily removed from the lower area of the bubble column reactor, and after flowing through the external heat exchanger circuit, recycled above the mixing element. In operation of the bubble column reactor, the liquid level is above the mixing element. After addition of the 2-methoxyethanol is completed, it is advantageous as a rule to leave the reaction mixture standing for a certain period so that it will undergo a secondary reaction in order to increase the conversion rate under the reaction conditions. As a rule, the reaction device is then expanded and emptied, and the reaction mixture is processed.

The continuous operation preferably takes place in a stirred vessel cascade, a trickle-bed reactor cascade, a cascaded bubble column reactor or a cascaded jet loop reactor.

FIG. 4a shows a highly simplified diagram of a possible reaction device for carrying out the continuous method using a stirred vessel cascade. This is composed of multiple stirred vessels connected in series. In general, the heat exchanger device of the individual stirred vessel can be located inside or outside the respective stirred vessel. Preferably, the respective heat exchanger device is located in an external circuit. The stirred vessel cascade can be operated both in suspension mode and in fixed-bed mode. It is preferably operated in suspension mode. In this case, the discharge of each suspension-catalyst-containing stirred vessel is preferably removed via a cross-flow filter in order to retain the suspension catalyst in the respective stirred vessel. At the beginning of the reaction, water and the catalyst are ordinarily first placed in the stirred vessel. Moreover, it is also possible at the beginning to place some 2-methoxyethanol e.g. in the first stirred vessel. The reaction device is now set to reaction conditions, i.e. in particular, it is brought to the desired temperature via mixing, and the desired oxygen partial pressure is set by pressurization of oxygen. 2-methoxyethanol, oxygen and water are now continuously supplied to the reaction device. Oxygen is preferably supplied to each individual stirred vessel. Excess gas can for example be discharged via pressure maintenance. The addition of 2-methoxyethanol takes placed in a spatially distributed manner in the first through the next-to-last stirred vessels. The last stirred vessel ordinarily serves as a secondary reaction zone, and 2-methoxyethanol is therefore generally not added to it. Water is preferably supplied only to the first stirred vessel. In each case, the reaction mixture is continuously removed from a stirred vessel and supplied to the following stirred vessel. The reaction mixture is continuously removed from the last stirred vessel, as a rule expanded, and processed.

A somewhat modified embodiment of a stirred vessel cascade is a cascaded stirred vessel. FIG. 4b shows a highly simplified reaction device for carrying out the continuous method using a cascaded stirred vessel. This comprises a plurality of stirred vessel compartments connected in series in a reaction vessel, each of which is provided with an overflow into the next compartment. In general, the heat exchanger device of an individual compartment can be inside or outside the respective compartment. Preferably, the respective heat exchanger device is located in an external circuit. The cascaded stirred vessel can be operated both in suspension mode and in fixed-bed mode. It is preferably operated in suspension mode. In this case, the discharge of each suspension-catalyst-containing compartment is preferably removed via a cross-flow filter in order to retain the suspension catalyst in the respective compartment. The addition of 2-methoxyethanol and water takes place in principle in the same manner as in the stirred vessel cascade. The last compartment is used for the secondary reaction and therefore does have any added 2-methoxyethanol. In contrast to the stirred vessel cascade, however, in the cascaded stirred vessel, the oxygen is ordinarily supplied at a central site. For this reason, central pressure maintenance is generally sufficient. The reaction mixture is continuously removed from the last compartment, as a rule expanded, and processed.

Figure 5:
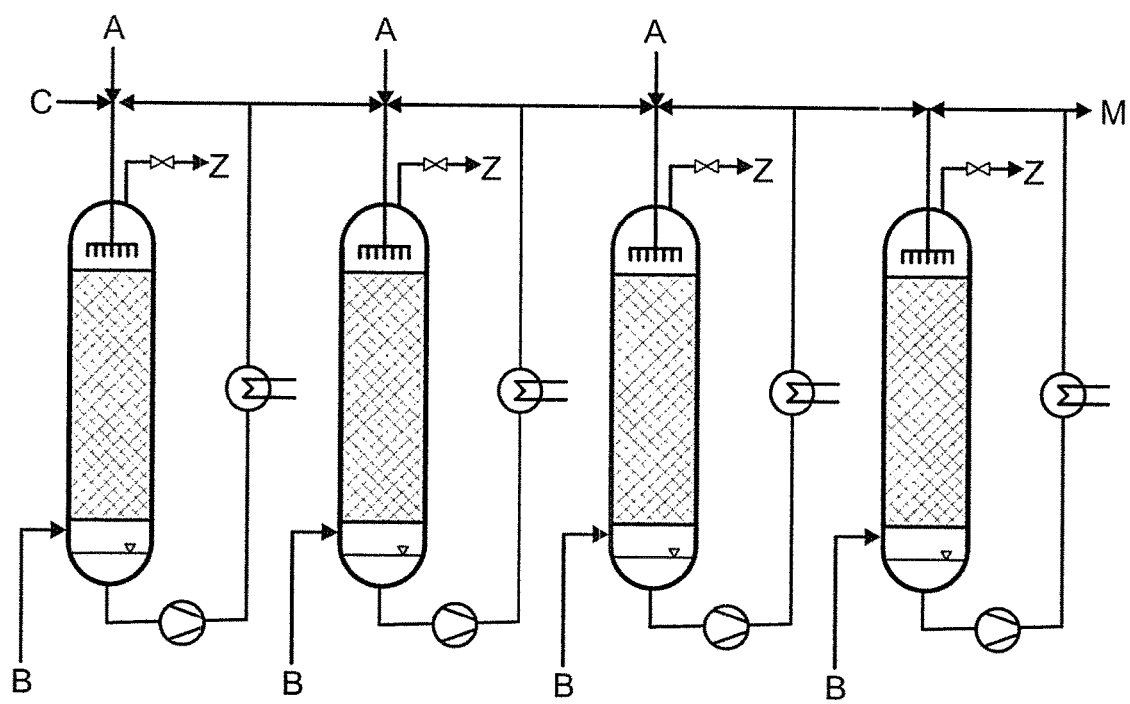

FIG. 5 shows a highly simplified diagram of a possible reaction device for carrying out the continuous method using a trickle-bed reactor cascade. This is composed of a plurality of trickle-bed reactors connected in series with a preferably external heat exchanger circuit. The basic structure and operation of a trickle-bed reactor has already been described for semi-continuous operation. The trickle-bed reactor cascade can also be operated both in suspension mode and in fixed-bed mode. Operation in fixed-bed mode is preferred. 2-methoxyethanol, oxygen and water are continuously supplied to the reaction device. Oxygen is preferably supplied to each individual trickle-bed reactor. Excess gas car for example be discharged via pressure maintenance. The addition of 2-methoxyethanol takes place in a spatially distributed manner in the first to the next-to-last trickle-bed reactors. The last trickle-bed reactor ordinarily serves as a secondary reaction zone, and 2-methoxyethanol is therefore generally not added to it. Water is preferably supplied only to the first trickle-bed reactor. In each case, the reaction mixture is continuously removed from a trickle-bed reactor and supplied to the following trickle-bed reactor. The reaction mixture is continuously removed from the last trickle-bed reactor, as a rule expanded, and processed.

Figure 6:
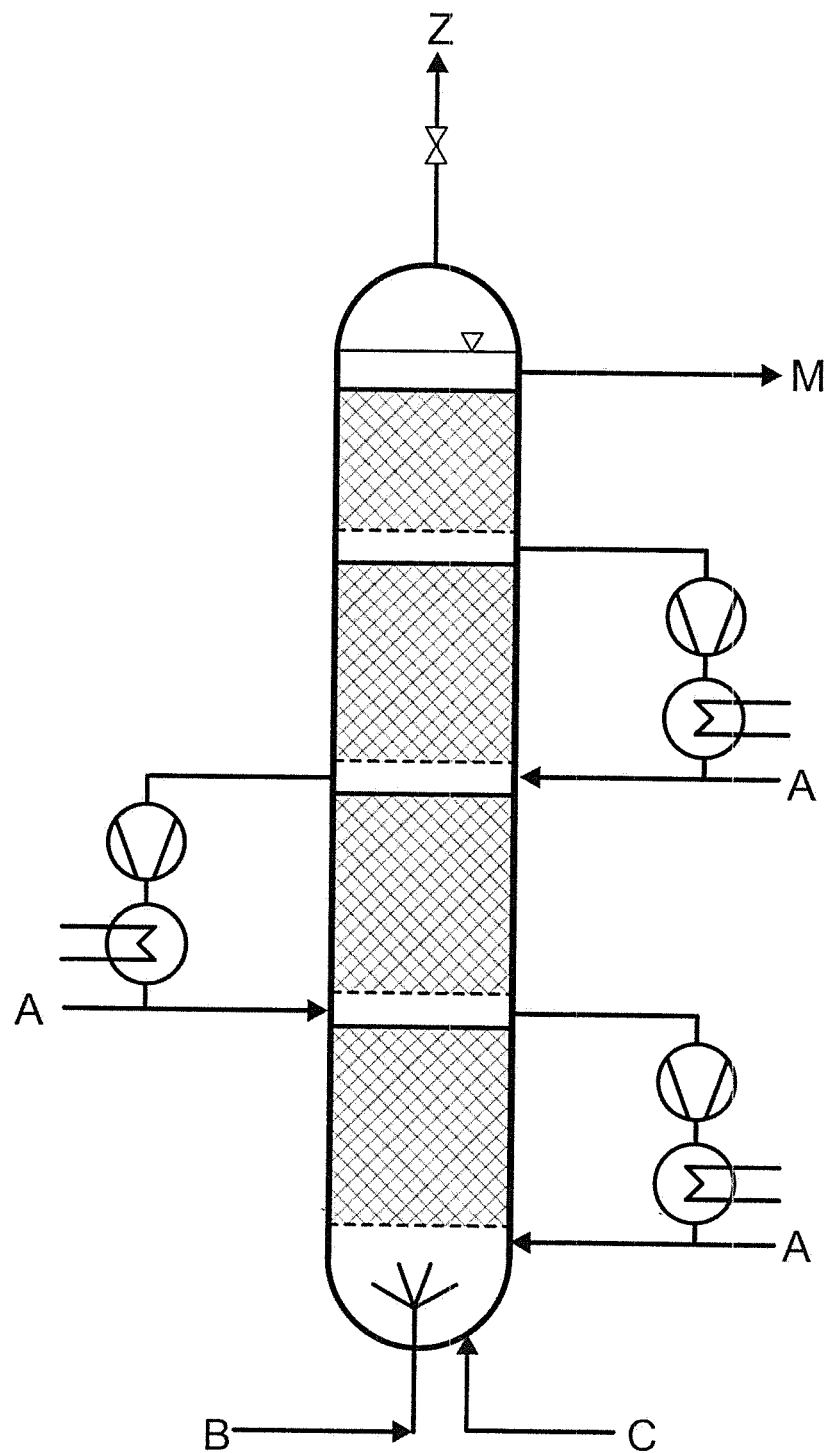

FIG. 6 shows a highly simplified diagram of a possible reaction device for carrying out the continuous method using a cascaded bubble column reactor. This has a construction similar to that of a bubble column reactor, but comprises a plurality of bubble column compartments connected in series. These are ordinarily separated from one another by suitable separating devices, for example perforated plates. Although these are permeable both to the oxygen rising from below and the liquid reaction mixture, they nevertheless provide flow resistance and reduce backmixing. Each of the individual compartments contains a heterogeneous catalyst. The cascaded bubble column reactor can be operated both in suspension mode and in fixed-bed mode. In the case of suspension mode, an inert filling or an inert packing respectively serves as a mixing element. Operation in fixed-bed mode is preferred. With the exception of the uppermost compartment, the reaction mixture is removed in each case above the respective mixing element, fed through a heat exchanger circuit, and recycled below the respective mixing element. The uppermost compartment serves as a secondary reaction zone and does not require cooling. 2-methoxyethanol, oxygen and water are continuously supplied to the reaction device. Oxygen is supplied via one or a plurality of nozzles below the first mixing element. The addition of 2-methoxyethanol takes place in a spatially distributed manner via the respective heat exchanger circuits of the first to next-to-last compartments. As the liquid phase is virtually completely backmixed in each compartment because of the heat exchanger circuit, 2-methoxyethanol can as a rule be added everywhere inside the respective compartment. Water is preferably supplied only below the first compartment. In operation of the cascaded bubble column reactor, the liquid level is above the uppermost mixing element. Excess gas can for example be discharged via pressure maintenance. The reaction mixture is continuously removed above the last mixing element, as a rule expanded, and processed.

Figure 7:
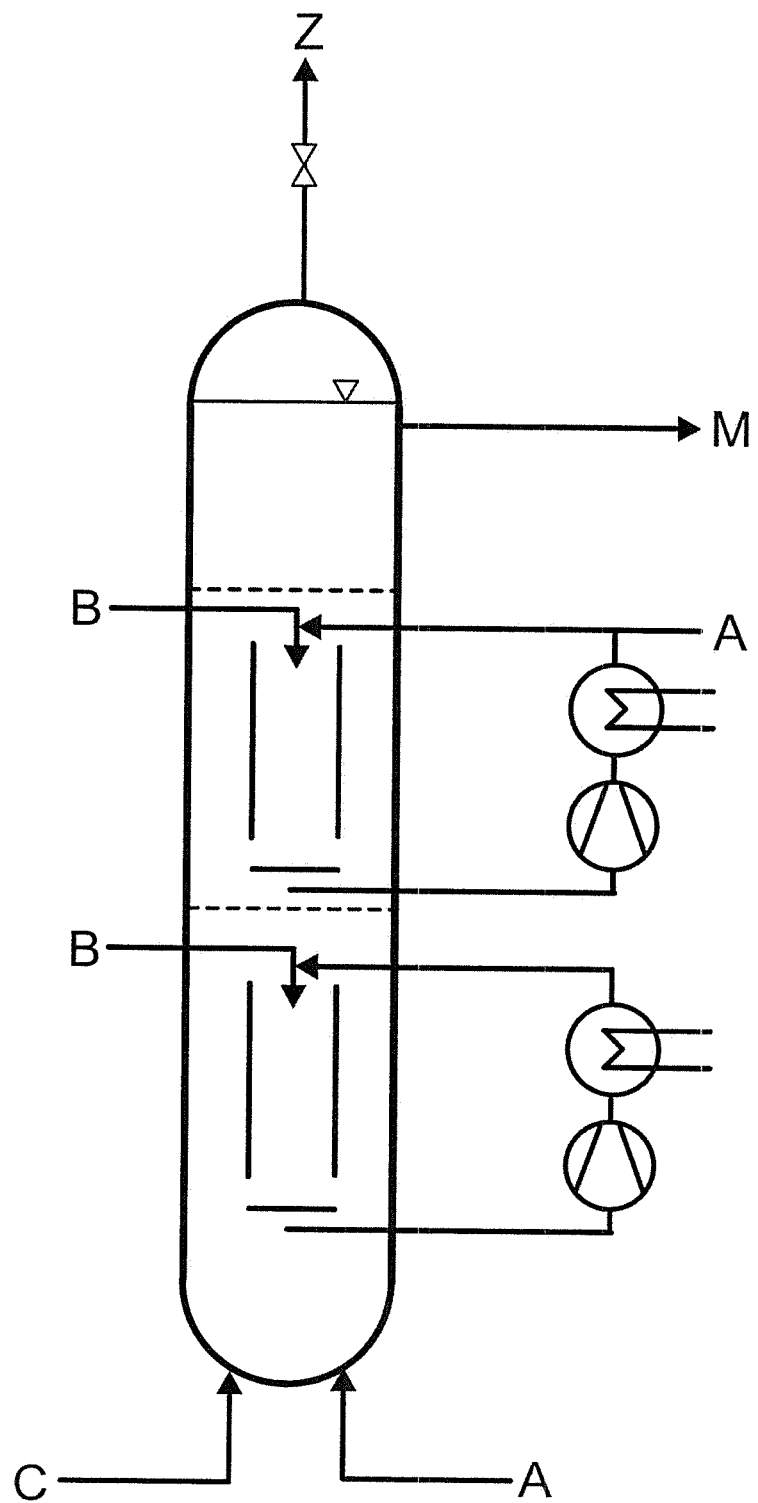

FIG. 7 shows a highly simplified diagram of a possible reaction device for carrying out the continuous method using a cascaded jet loop reactor. This has a construction similar to that of a jet loop reactor, but comprises a plurality of jet loop compartments connected in series, wherein the uppermost compartment is equipped without jet loop internals and serves as a secondary reaction zone. The individual compartments are ordinarily separated from one another by suitable separating devices, for example perforated plates. These provide flow resistance and reduce back mixing. As is common for jet loop reactors, each of the jet loop internals comprises a jet nozzle, a pulse tube, and a deflecting plate. In operation of the cascaded jet loop reactor, the reaction mixture is removed in each case below the deflecting plate, fed through the heat exchanger circuit, and recycled together with freshly supplied oxygen via the jet nozzle located in the pulse tube, thus ensuring intensive mixing inside the respective jet loop compartment. Each of the individual compartments contains a heterogeneous catalyst. The cascaded jet loop reactor can be operated both in suspension mode and in fixed-bed mode. Operation in fixed-bed mode is preferred. In the case of fixed-bed mode, the catalyst is fixed in the ring-shaped area between the pulse tube and the reactor wall. In the secondary reaction, in the simplest case, the catalyst is present in the form of a classical fixed bed without surrounding jet loop internals (as shown in the figure). Alternatively, however, jet loop internals can also be present together with an external circulation pump in the secondary reaction zones, and the catalyst can be fixed in the ring-shaped area between the pulse tube and the reactor wall. In the case of suspension mode, one must ensure in every case that the secondary reaction zone is also actively mixed. This can be achieved for example by means of a mechanical stirrer or jet loop internals with an external circulation pump. Regardless of whether the cascaded jet loop reactor is operated in suspension or fixed-bed mode, 2-methoxyethanol is supplied to the respective jet loop compartments, with the exception of the secondary reaction zone, in a spatially distributed manner. As the liquid phase is virtually completely backmixed in each jet loop compartment because of the heat exchanger circuit and the intensive mixing, 2-methoxyethanol can as a rule be added everywhere inside the respective compartment. Water is preferably supplied only below the first compartment. In operation of the cascaded jet loop reactor, the liquid level is above the uppermost compartment. Excess gas can for example be discharged via pressure maintenance. The reaction mixture is continuously removed from the upper area of the uppermost compartment, but below the liquid level, as a rule expanded, and processed.

The method according to the invention allows the production of 2-methoxyacetic acid of high selectivity, yield, and purity. The method is simple to carry out and is based on the readily available ingredient 2-methoxyethanol. The 2-methoxyacetic acid obtainable according to the invention is obtained with significantly higher purity than the 2-methoxyacetic acid produced according to the prior art. In particular, the 2-methoxyacetic acid obtainable according to the invention contains sharply lower amounts of the undesirable byproduct methoxyacetic acid-2-methoxyethylester. Moreover, despite higher selectivity for 2-methoxyacetic acid and reduced formation of methoxyacetic acid-2-methoxyethylester, the method according to the invention allows a more concentrated operating mode with respect to 2-methoxyethanol and 2-methoxyacetic acid and thus the use of a smaller reactor volume. The reduced formation of byproducts, in particular methoxyacetic acid-2-methoxyethylester, and the more concentrated operating mode make it possible to carry out processing using simpler equipment and in a more energy-efficient manner. In addition, the 2-methoxyacetic acid obtained has a lower color index.

EXAMPLES

Examples 1 to 5

375 g of water and 25.6 g of a Pt/C catalyst (source: Sigma-Aldrich, 5 wt % of Pt based on the carbon carrier, 1446 $m^2$/g BET surface area, Pt particles in the range of 1-5 nm) were first placed in a 1.6-l reaction calorimeter with a hollow shaft gassing stirrer, the mixture was heated to 50° C. under stirring at 1000 rpm, and a total pressure of 0.3 MPa was set by adding oxygen. After this, 125 g of 2-methoxyethanol was either placed in the calorimeter (example 1, formally corresponding to addition within 0 h) or supplied at a constant rate over a period of 1.5 h (example 2) to 8 h (example 5). In the case of example 1 (0 h), the 125 g of 2-methoxyethanol was added immediately at the beginning of time measurement. In each case, by means of pressure-controlled addition of oxygen, the total pressure in the reaction calorimeter was maintained at 0.3 MPa abs throughout the entire reaction time. By means of the pressure-controlled supply, oxygen consumption was simultaneously detected, and the conversion rate of 2-methoxyethanol over the course of the reaction was thus indirectly determined. Parallel to this, the amount of heat currently produced was detected in each case. After completion of 2-methoxyethanol addition, the reaction calorimeter was allowed to stand under the set conditions until a 2-methoxyethanol conversion rate of 95% was reached in each case. After this, the reaction calorimeter was cooled to room temperature and expanded to atmospheric pressure, and the removed reaction mixture was freed of the catalyst by filtration.

The filtered reaction mixture was then purified in order to remove water and unreacted 2-methoxyethanol in a continuously-operated Sambay evaporator with a surface area of 0.046 $m^2$ at 50° C., 25 hPa abs and at an addition rate of 1 mL of reaction mixture per minute. The purified bottom product was removed and analyzed without further distillative purification by quantitative gas chromatography using 1,4-dioxane as an internal standard, and the color index according to APHA was determined. In each of the examples, the product contained a maximum of 0.3 wt % of water and a maximum of 0.3 wt % of 2-methoxyethanol. All further results obtained are shown in Table 1.

The value CA is calculated from the total mass of 2-methoxyethanol and the total mass of water used. The value CA is therefore the same for all five examples.

The maximum CR was determined from the course over time of the conversion of 2-methoxyethanol, wherein the stoichiometry of the reaction was of course taken into consideration.

The examples show that formation of the undesirable methoxyacetic acid-2-methoxyethylester decreases as the maximum CR drops. The color index according to APHA also decreases as the maximum CR drops. Both the value CA and thus the masses of the total 2-methoxyethanol and water added, as well as the maximum required reactor volume, were the same for all five examples. With the same reaction batch size and identical reactor volume, it was possible by addition according to the invention of 2-methoxyethanol to obtain a reaction mixture of significantly greater purity. In comparative example 1 according to the prior art, the reaction mixture contained 2.6 wt % of undesirable methoxyacetic acid-2-methoxyethylester, in example 3 according to the invention, it contained only 0.9 wt %, and in example 5 according to the invention, the remaining content was as low as 0.5 wt %.

With the decrease in maximum CR, the maximum amount of thermal energy produced also dropped significantly. This value was extremely high at 457 W/kg in comparison example 1, in example 3 according to the invention for example only 81 W/kg, and in example 5 according to the invention, it was as low as only 30 W/kg. In accordance with this significant decrease in the amount of heat produced, in the method according to the invention, even sharply lower cooling performance is sufficient, which makes it possible to use a smaller cooler having a significantly lower peak cooling performance.

Example 6

Example 3 was repeated, using in example 6 as a reactor a 1.5 liter stirred vessel (CSTR) with a hollow shaft gassing stirrer, with the bottom outlet thereof being equipped with a sintered glass filter so that the catalyst would be left in the reactor each time it was emptied. On completion of the experiment, i.e. after a 2-methoxyethanol conversion rate of 95% was reached, the reaction mixture was removed via the sintered glass filter and analyzed as in example 3 by gas chromatography, and its color index according to APHA was determined. The catalyst remaining in the reactor was reused in the next batch under the conditions of example 3. A total of 20 such batches were processed with the same catalyst load. Activity and selectivity remained constant within the range of measurement accuracy.

Example 6 shows that in the method according to the invention, the catalyst can be reused over many semi-continuous cycles, and even after 20 cycles, no loss of activity or selectivity can be detected.

TABLE 1

| Example | Unit | 1 (comparison) | 2 (comparison) | 3 (invention) | 4 (invention) | 5 (invention) |
|---|---|---|---|---|---|---|
| Duration of addition of 2ME[#1] | [h] | 0 | 1.5 | 3 | 5 | 8 |
| Reaction time until reaching 95% 2ME conversion rate[#1] | [h] | 6.7 | 8 | 10 | 11.7 | 13.2 |
| CA | [g/g] | 0.25 | 0.25 | 0.25 | 0.25 | 0.25 |

TABLE 1-continued

| Example | Unit | 1 (comparison) | 2 (comparison) | 3 (invention) | 4 (invention) | 5 (invention) |
|---|---|---|---|---|---|---|
| Maximum concentration of 2ME[#1] in the reaction mixture | [wt %] | 25.0 | 20.7 | 17.2 | 13.9 | 11.7 |
| Maximum CR | [g/g] | 0.250 | 0.215 | 0.188 | 0.158 | 0.136 |
| Maximum (CR · 100)/CA | [%] | 100 | 86.0 | 75.2 | 63.2 | 54.4 |
| Maximum heat output produced during reaction | [W/kg] | 457 | 252 | 81 | 34 | 30 |
| Content of ME2MEE[#3] based on content of 2MAA[#2] in purified reaction mixture | [wt %] | 2.6 | 1.3 | 0.9 | 0.7 | 0.5 |
| Color index (APHA) of purified reaction mixture | | >60 | >60 | <50 | <50 | <50 |

[#1] 2ME = 2-methoxyethanol
[#2] 2MAA = 2-methoxyacetic acid
[#3] ME2MEE = methoxyacetic acid-2-methoxyethylester

The invention claimed is:

1. A method for producing 2-methoxyacetic acid comprising oxidizing 2-methoxyethanol in a reaction device using oxygen at a temperature of 20 to 100° C. and an oxygen partial pressure of 0.01 to 2 MPa in the presence of water and a heterogeneous catalyst containing platinum, wherein the method is carried out semi-continuously or continuously and in that the addition of 2-methoxyethanol to the reaction device is temporally and spatially selected such that temporally and spatially, in the liquid phase containing 2-methoxyethanol and 2-methoxyacetic acid in the reaction device, the quotient of CR/CA is constantly ≤0.80, wherein CR is defined as $$CR = \frac{C(2-\text{methoxyethanol reactor})}{C(2-\text{methoxyethanol reactor}) + C(\text{water reactor})},$$

and wherein C(2-methoxyethanol reactor) denotes the mass of 2-methoxyethanol per volume element of the liquid phase containing 2-methoxyethanol and 2-methoxyacetic acid, and C(water reactor) denotes the mass of water per volume element of the liquid phase containing 2-methoxyethanol and 2-methoxyacetic acid, in the semi-continuous method, CA is defined as $$CA = \frac{MT(2-\text{methoxyethanol total mass})}{MT(2-\text{methoxyethanol total mass}) + MT(\text{water total mass})},$$

wherein MT(2-methoxyethanol total mass) denotes the total mass of 2-methoxyethanol used in the semi-continuous method, and MT(water total mass) denotes the total mass of water used in the semi-continuous method, and in the semi-continuous method, CA is defined as $$CA = \frac{MF(2-\text{methoxyethanol mass flow})}{MF(2-\text{methoxyethanol mass flow}) + MF(\text{water mass flow})},$$

wherein MF(2-methoxyethanol mass flow) denotes the mass flow of 2-methoxyethanol supplied to the reaction device, and MF(water mass flow) denotes the mass flow of water supplied to the reaction device.

2. The method as claimed in claim 1, wherein the addition of 2-methoxyethanol to the reaction device is temporally and spatially selected such that temporally and spatially, in the liquid phase containing 2-methoxyethanol and 2-methoxyacetic acid in the reaction device, the quotient of CR/CA is constantly ≤0.70.

3. The method as claimed in claim 1, wherein a ratio by weight of water to 2-methoxyethanol of 1 to 5 is used, wherein this is based in the semi-continuous method on the total mass of water and 2-methoxyethanol used and in the continuous method on the mass flows of water and 2-methoxyethanol supplied to the reaction device.

4. The method as claimed in claim 1, wherein a heterogeneous catalyst containing 0.1 to 10 wt % of platinum on carbon is used.

5. The method as claimed claim 1, wherein the method is carried out semi-continuously, and 2-methoxyethanol is supplied to the reaction device over a period of 1 to 10 h.

6. The method as claimed in claim 1, wherein the method is carried out continuously and 2-methoxyethanol and water are supplied to the reaction device such that the mass flow of 2-methoxyethanol and water based on the total reactor volume in the reaction device is 0.05 to 0.5 per h.

7. The method as claimed in claim 1, wherein 80 to 99% of the 2-methoxyethanol used is reacted.

8. The method as claimed in claim 1, wherein the method is carried out semi-continuously and the reaction comprises a reactor from the group of a stirred vessel, a trickle-bed reactor, and a bubble column reactor.

9. The method as claimed in claim 1, wherein the method is carried out continuously and the reaction comprises a reactor selected from the group consisting of a stirred vessel cascade, a trickle-bed reactor cascade, a cascaded bubble column reactor, and a cascaded jet loop reactor.

10. The method as claimed in claim 1, wherein the low boilers water and 2-methoxyethanol are removed by evaporation from the reaction mixture obtained.

* * * * *